United States Patent
Nakamura et al.

(10) Patent No.: US 6,310,236 B1
(45) Date of Patent: Oct. 30, 2001

(54) PROCESS FOR PREPARING α-HYDROXYCARBOXYLATE

(75) Inventors: Kenichi Nakamura; Futoshi Kawataka; Kazuhiro Yamada; Wataru Ueno, all of Ibaraki-ken (JP)

(73) Assignee: Mitsubishi Gas Chemical Company, Tokyo (JP)

( * ) Notice: Subject to any disclaimer, the term of this patent is extended or adjusted under 35 U.S.C. 154(b) by 0 days.

(21) Appl. No.: 09/274,863

(22) Filed: Mar. 23, 1999

(51) Int. Cl.$^7$ .................................................. C07C 69/66
(52) U.S. Cl. ..................... 560/179; 560/212; 560/215; 560/96
(58) Field of Search .................... 560/179, 215, 560/212, 96

(56) References Cited

U.S. PATENT DOCUMENTS

| | | | | |
|---|---|---|---|---|
| 2,041,820 | * | 5/1936 | William et al. | 560/179 |
| 4,055,590 | * | 10/1977 | Gruber et al. | 560/179 |
| 4,161,609 | * | 7/1979 | Cramer | 560/215 |
| 4,450,112 | * | 5/1984 | Wreford | 554/154 |
| 4,464,539 | * | 8/1984 | Hashimoto et al. | 560/212 |
| 4,613,684 | * | 9/1986 | Aoyama et al. | 560/179 |
| 4,990,651 | * | 2/1991 | Ikarashi et al. | 560/103 |

OTHER PUBLICATIONS

Databas WPI Derwent Publications Ltd., AN 1995–380018, Oct. 9, 1995.
Database WPI, Derwent Publications Ltd., AN 1996–205484, Mar. 19, 1996.
Database WPI, Derwent Publications Ltd., AN 1995–070252, Dec. 20, 1994.

* cited by examiner

*Primary Examiner*—Paul J. Killos
*Assistant Examiner*—Taylor V. Oh
(74) *Attorney, Agent, or Firm*—Antonelli, Terry, Stout & Kraus, LLP

(57) ABSTRACT

There is herein disclosed a process for efficiently preparing, from an α-hydroxycarboxylic amide and an alcohol in an industrially advantageous manner, an α-hydroxycarboxylate which is useful as any of raw materials for solvents, food additives, perfumes, various organic medicines and the like.

According to the present invention, there is provided a process for preparing an α-hydroxycarboxylate which comprises the step of reacting an α-hydroxycarboxylic amide and an alcohol in the presence of a catalyst in a liquid phase, while an ammonia concentration in a reaction solution is maintained at 0.1% by weight or less by discharging generated ammonia as a gas into a gaseous phase.

18 Claims, 1 Drawing Sheet

PROCESS FOR PREPARING α-HYDROXYCARBOXYLATE

BACKGROUND OF THE INVENTION

1. Field of the Invention

The present invention relates to a process for preparing an α-hydroxycarboxylate. More specifically, the present invention relates to a process for efficiently preparing, from an α-hydroxycarboxylic amide and an alcohol in an industrially advantageous manner, an α-hydroxycarboxylate which is useful as any of raw materials for solvents, food additives, perfumes, medicines, agricultural chemicals, industrial chemicals, degradable polymers and α-amino acids.

2. Description of the Prior Art

It is known that α-hydroxycarboxylates are industrially extremely important compounds, and for example, lactates which are one kind of α-hydroxycarboxylates are used as high-boiling solvents and as raw materials for food additives, perfumes, medicines, agricultural chemicals and degradable polymers. In addition, the α-hydroxycarboxylates can be used as solvents, as raw materials for the production of methacrylates, particularly methyl methacrylate by dehydration, and as raw materials for the production of α-amino acids by aminolysis.

As techniques for manufacturing the α-hydroxycarboxylates, some methods are known from former days which comprise reacting an alcohol with a nitrile in the presence of an acid catalyst. For example, as preparation techniques of lactates, Japanese Patent Publication Nos. 8061/1955 and 2333/1965 disclose methods which comprise dissolving lactonitrile in an alcohol and water, adding sulfuric acid to the solution to carry out hydrolysis and esterification, and then introducing an alcohol vapor into the resultant mixture. With regard to α-hydroxyisobutyrates, there are known methods for preparing them by reacting acetone cyanohydrin with an alcohol in the presence of an acid catalyst, and these methods are disclosed in, for example, U.S. Pat. No. 2,041,820 and Japanese Patent Application Laid-Open No. 230241/1992. These reactions are exothermic and can spontaneously proceed, and for the reason, a manufacturing apparatus is simpler as compared with other methods which will hereinafter be described. However, since the acid catalyst is used, an anticorrosive material is required to be used, and what is worse, a large amount of a salt is disadvantageously produced as a waste product.

As techniques for the manufacture of the α-hydroxycarboxylates, there are methods which comprise reacting an α-hydroxycarboxylic amide with an ester. For example, Japanese Patent Application Laid-Open Nos. 178792/1993 and 145106/1994 disclose methods which comprise reacting α-hydroxyisobutyric amide with a formate to obtain an α-hydroxyisobutyrate. This reaction is an exchange reaction between the amide and the ester and hence it is neither noticeably exothermic nor endothermic, so that any anticorrosive material is not necessary. However, these techniques have a drawback that the reaction proceeds merely until an equilibrium composition of the amide and the ester has been reached.

Furthermore, known is a method which comprises directly reacting an α-hydroxycarboxylic amide with an alcohol to prepare the α-hydroxycarboxylate. This method is characterized in that any salt to be discarded is not produced, and any upper limit of a conversion of the raw material amide is not present in principle. For example, Japanese Patent Application Laid-Open No. 3015/1977 describes a method in which the reaction is carried out in the presence of a metal carboxylate, while the reaction system is intermittently purged with a gas. In this method, however, a yield is low and a large amount of by-products is formed, and for these reasons, the disclosed method is not practical.

In addition, Japanese Patent Application Laid-Open Nos. 345692/1994, 258154/1995 and 73408/1996 suggest methods which comprise performing a reaction in the presence of an insoluble solid acid catalyst or a metallic catalyst, while a large amount of a nitrogen gas is fed and generated ammonia is discharged. According to investigation by the present inventors, it has been apparent that in order to prepare the α-hydroxycarboxylate in a high yield in accordance with each of these methods, a large amount of nitrogen is necessary. Thus, for the sake of the collection of ammonia from the discharged gas, a good deal of energy is required. Furthermore, the amount of the catalyst to be used increases, a long period of time is required for the reaction, and a large amount of by-products is formed. Accordingly, the disclosed methods are not industrially practical.

SUMMARY OF THE INVENTION

The present invention has been developed under such circumstances with the intention of overcoming the above-mentioned drawbacks of conventional preparation methods of α-hydroxycarboxylates, and an object of the present invention is to provide a process for efficiently preparing an α-hydroxycarboxylate from an α-hydroxycarboxylic amide and an alcohol in an industrially advantageous manner.

The present inventors have intensively investigated on a reaction of the following formula which is carried out in a liquid phase in order to achieve the above-mentioned object, and as a result, it has been found that when the amount of ammonia present in a reaction solution is decreased, a reaction rate can be increased and a high conversion and selectivity can be obtained, and moreover, the formation of by-products can be controlled. The reaction can be represented by the following formula (1):

$$R^1R^2C(OH)CONH_2 + R^3OH = R^1R^2C(OH)COOR^3 + NH_3 \quad (1)$$

wherein $R^1$ and $R^2$ are each a hydrogen atom or an alkyl group; and $R^3$ is an alkyl group or an aralkyl group.

Since this reaction is an equilibrium reaction, the reaction toward a production side naturally proceeds by distilling off ammonia from a production system. As described above, it is known that a pressure rise occurs owing to the production of ammonia similarly in conventional techniques and the equilibrium moves to the production side by discharging intermittently or partially the pressure. However, ammonia dissolves in the alcohol and the α-hydroxycarboxylate under the pressure, and hence an ammonia concentration in the liquid phase cannot be decreased only by this operative procedure.

The present inventors have found that when the reaction is carried out while generated ammonia is discharged as a gas into a gaseous phase by bringing the reaction solution into a boiling state or bubbling an inert gas in the reaction solution to maintain the ammonia concentration in the reaction solution at a low level, a reaction rate can be increased and a high conversion and selectivity can be obtained, and moreover, the formation of by-products can be inhibited. In particular, the present inventors have found that maintaining the ammonia concentration in the reaction solution at 0.1% by weight or less is effective to inhibit the formation of the by-products, which has not been suggested so far by anyone.

With regard to the by-products, if ammonia is present in the reaction solution, as shown by the following formula (2), a quaternary amine salt of an α-hydroxycarboxylic acid is produced from the α-hydroxycarboxylate which is the desired product and ammonia, and an α-hydroxycarboxylic (N-alkyl)amide is then generated via the Hofmann gradation:

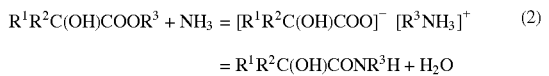

$$R^1R^2C(OH)COOR^3 + NH_3 = [R^1R^2C(OH)COO]^- [R^3NH_3]^+ \quad (2)$$
$$= R^1R^2C(OH)CONR^3H + H_2O$$

wherein $R^1$, $R^2$ and $R^3$ are as defined above.

If the ammonia concentration in the reaction solution is more than 0.1% by weight, the production of this α-hydroxycarboxylic(N-alkyl)amide increases, so that the selectivity noticeably decreases.

In addition, the present inventors have found that if the ammonia concentration in the reaction solution is high, not only the equilibrium reaction scarcely proceeds toward the production system, but also ammonia is coordinated with or adsorbed on a catalyst. Consequently, the coordination or the adsorption of the α-hydroxycarboxylic amide which is the raw material is noticeably disturbed, so that the decline of the reaction rate takes place. That is to say, if the ammonia concentration in the reaction solution is more than 0.1% by weight, the reaction does not proceed up to an equilibrium conversion any more, so that an apparent reaction rate is low and the reaction stops inconveniently.

As a means for maintaining the ammonia concentration in the reaction solution at 0.1% by weight or less, it can be contrived to intermittently or partially discharge a pressure rise brought about by generated ammonia, but such a contrivance is insufficient. The present inventors have found that the above-mentioned maintenance of the ammonia concentration at the low concentration can easily be achieved by continuously feeding the alcohol to the reaction solution phase, while the reaction solution is brought into a boiling state or the bubbling of an inert gas is performed to distill off ammonia and the alcohol.

The present invention has been completed on the basis of this knowledge.

That is to say, the present invention is directed to a process for preparing an α-hydroxycarboxylate which comprises the step of reacting an α-hydroxycarboxylic amide and an alcohol in the presence of a catalyst in a liquid phase, while an ammonia concentration in a reaction solution is maintained at 0.1% by weight or less by discharging generated ammonia as a gas into a gaseous phase.

A preferable manner for maintaining the ammonia concentration in the reaction solution at 0.1% by weight or less comprises either or both of steps of bringing the reaction solution into a boiling state and bubbling an inert gas in the reaction solution to discharge generated ammonia as a gas into a gaseous phase. Another preferable manner for maintaining the ammonia concentration comprises the step of continuously feeding the alcohol to the reaction solution while generated ammonia is continuously discharged together with the alcohol as the gas into the gaseous phase.

Figure 1:
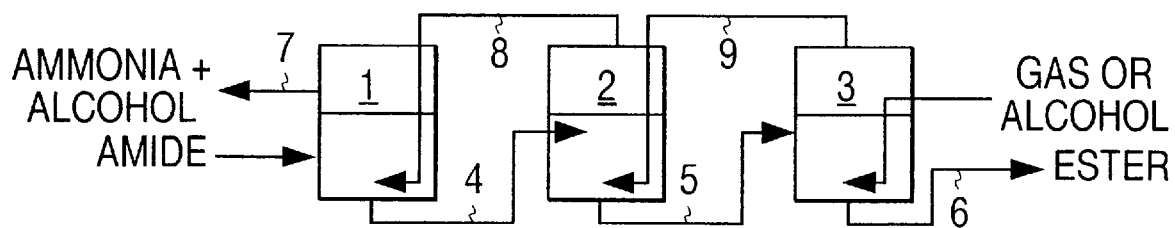
FIG. 1 is a schematic view of one embodiment of a reaction apparatus for use in the practice of the present invention in which independent reactors are connected.

In these drawings, reference numerals represent the following parts:

| | |
|---|---|
| 1 | First reactor |
| 2 | Second reactor |
| 3 | Third reactor |
| 4, 5, 6 | Liquid conduits |
| 7, 8, 9 | Gas conduits |
| 10 | Methanol |
| 11 | Liquid feed pump |
| 12 | Lower reactor |
| 13 | Gas conduit |
| 14 | Liquid conduit |
| 15 | Valve for constantly keeping the height of a liquid surface in the lower reactor |
| 16 | Cooler |
| 17 | Bottom receiver |
| 18 | Gas conduit |
| 19 | Condenser |
| 20 | Condensed liquid receiver |
| 21 | Valve |
| 22 | Liquid feed pump |
| 23 | Raw material solution (a mixed solution of an α-hydroxybutyric amide, titanium isopropoxide and methanol) |
| 24 | Upper reactor |

DESCRIPTION OF PREFERRED
EMBODIMENTS OF THE INVENTION

A process for preparing an α-hydroxycarboxylate of the present invention comprises the step of reacting an α-hydroxycarboxylic amide with an alcohol, which are raw materials, in the presence of a catalyst in a liquid phase.

In this process, typical examples of the α-hydroxycarboxylic amide which can be used as a raw material include lactamide and α-hydroxyisobutyric amide, but they are not restrictive. Typical examples of the alcohol include methanol, ethanol, propanol, butanol, 2-ethylhexanol, glycidyl alcohol and benzyl alcohol, and above all, methanol is suitable. The amount of the alcohol to be used is preferably in the range of 1 to 50 mol, more preferably 2 to 20 mol per mol of the α-hydroxycarboxylic amide.

Reaction temperature is usually selected in the range of 100 to 250° C., preferably 120 to 230° C. If the reaction temperature is lower than 100° C., a reaction rate is too low to be practical, and if it is higher than 250° C., amounts of by-products such as α-alkoxycarboxylates, α-hydroxycarboxylic acid and olefin derivatives which are dehydrated products increase inconveniently. In the reaction, it is preferred that water is not present in the reaction system, but if the amount of water is 3 mol or less per mol of the α-hydroxycarboxylic amide, the reaction can proceed.

Reaction pressure can suitably be decided in consideration of the kind and the amount of alcohol to be used, the reaction temperature and the like, but in general, it is in the range of 1 to 100 atm, preferably 5 to 50 atm. The reaction can also be carried out in the presence of a solvent. Furthermore, a reaction system may be either of a batch system or a continuous system.

In the process of the present invention, any of soluble metallic catalysts and solid catalysts can be used, and no particular restriction is put on them. For example, the catalyst can suitably be selected in compliance with the situation from the group consisting of (1) soluble metallic complexes, (2) metallic trifluoromethanesulfonates, (3) insoluble metallic oxides and (4) insoluble metals.

Preferable examples of the soluble metallic complexes (1) include, but are not limited to, soluble metallic complexes comprising either or both of titanium and tin, and the α-hydroxycarboxylic amide. In the case that titanium is selected as a metal source, an alkoxylate such as titanium tetraisopropoxide may directly be fed to the reaction system to form a soluble complex comprising titanium and the α-hydroxycarboxylic amide in the system, or alternatively, another complex may be formed from titanium tetraisopropoxide and the α-hydroxycarboxylic amide outside the reaction system, and the thus formed complex may then be added to the reaction system.

Also in the case that tin is selected as the metal source, the same technique as described above is applicable. For example, an alkyl tin compound may directly be fed to the reaction system to form a soluble complex comprising tin and the α-hydroxycarboxylic amide in the reaction system. In this case, an example of the alkyl tin compound is a tin compound bonded to a substituent such as an n-butyl group. A metallic compound which is a catalyst material precursor for use in this step is not particularly restricted.

The above-mentioned metallic trifluoromethanesulfonate (2) (which is also called "a metallic triflate") may be soluble or insoluble, and its example is a metallic triflate which includes one or more metallic elements selected from the group consisting of elements in the groups 1, 2, 3, 4, 11, 12, 13 and 14 in the periodic table and which has a triflate as a ligand. Particularly preferable are the metallic triflates each including one or more elements selected from the group consisting of Na, Li, K, Mg, Ca, Sr, Ba, Sc, Y, La, Pr, Nd, Sm, Eu, Gd, Dy, Ho, Er, Tm, Yb, Lu, Hf, Cu, Ag, Zn, Cd, Hg, B, Al, Ga, In, Tl, Si, Ge, Sn and Pb.

Japanese Patent Application Laid-Open No. 3015/1977 describes that a soluble metallic complex including a carboxylate as an anion can accelerate an alcoholysis, but when this metallic triflate is used, the reaction can be more accelerated and a higher reaction rate can be obtained than in the case that the metallic carboxylate is used.

The above-mentioned soluble metallic complex (1), particularly a titanium homogeneous system catalyst is highly hydrolytic, and hence, if it is used, a water content in the raw material system is required to be controlled. On the contrary, the triflate of a lanthanoide can be prepared by a hydrothermal synthesis in an aqueous solution. Since the lanthanoide itself is also less hydrolytic, the metallic triflate catalyst is neither hydrolyzed nor deactivated even in the system including water, so that the reaction can be advanced. Thus, the metallic triflate catalyst has a large advantage and is industrially suitable.

Furthermore, a preferable example of the above-mentioned insoluble metallic oxide (3) is a metallic oxide including at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi.

In addition, a preferable example of the above-mentioned insoluble metal (4) is an insoluble metal including at least one element selected from the group consisting of Ti, Zr, Hf, V, Nb, Ta, Cr, Mo, W, Fe, Co, Ni, Cu, Ga, In, Bi and Te.

These catalyst may be used singly or in a combination of two or more thereof, and either usage of the soluble catalyst and the insoluble catalyst can suitably be decided in accordance with a reaction type. Furthermore, the insoluble catalyst may be used in the form of a slurry or a molded article, but this form can suitably be selected in accordance with its usage.

In the process of the present invention, the reaction is required to be carried out while the ammonia concentration in the reaction solution is maintained at 0.1% by weight or less by discharging generated ammonia as a gas into a gaseous phase. As just described, when the reaction is carried out maintaining the ammonia concentration in the reaction solution at 0.1% by weight or less, a reaction rate can be enhanced and a high conversion and selectivity can be obtained, and the amount of by-products can also be inhibited.

As an advantageous technique for maintaining the ammonia concentration in the reaction solution at 0.1% by weight or less, there is, for example, (1) a method which comprises either or both of the step of bringing the reaction solution into a boiling state and the step of bubbling an inert gas therein to discharge generated ammonia as the gas into the gaseous phase; or (2) a method which comprises continuously feeding the alcohol to the reaction solution, and simultaneously continuously discharging generated ammonia together with the alcohol as the gas into the gaseous phase.

Alternatively, it is also advantageous that as the reaction apparatus, a gas stripping column is used, and the amide and the alcohol which are raw materials are fed to this column and the reaction is then carried out in the gas stripping column while ammonia is distilled off. Since the compositions of the solution and the gas in the reaction column continuously or discontinuously change, it is possible to increase the conversion of the amide while the amount of the distilled alcohol is maintained at a relatively low level. Here, the gas stripping column means a column which can industrially be used to separate and discharge a desired component from a mixed solution into a gas. The discharge of the gas is theoretically the reverse operation of gas absorption, and hence there can often be utilized a column which can be used for the gas absorption.

Various types of gas stripping columns are prevalent, and both of a liquid dispersion type and a gas dispersion type are applicable. Examples of the liquid dispersion type include a packed column, a wetted-wall column, a liquid column tower and a spray tower. Examples of the gas dispersion type include a bubble column, a gas blowing type stirrer and a plate column. Among them, the packed column, the bubble column and the plate column are preferable. In the packed column, any of a random packing, an ordered packing can be used. Moreover, a solid catalyst can be molded and the thus molded articles can then be used as the packing. In the bubble column, either of a nozzle type or a porous plate can be used, and the bubble column may be filled with a certain kind of packing.

In the gas dispersion type column, the stream of the slurry-like raw material is relatively easy, and this kind of column is suitable for a case where the insoluble catalyst is used. When the homogeneous system catalyst is used, either of the liquid dispersion type and the gas dispersion type is acceptable. As the gas for use therein, not only an uncondensable gas such as nitrogen but also a condensable gas such as the vapor of the alcohol can be used. A gas generated by heating the lower portion of the column to vaporize the internal liquid may also be used. It is desirable that the liquid and the gas flow in the state of counterflow, because in such a case, ammonia can more efficiently be stripped than in the case of parallel flow. For the sake of the counterflow, it is recommendable that the gas is fed or generated through the lower portion of the gas stripping column and the raw material amide is fed through the upper portion thereof.

Furthermore, in a preferable embodiment for the practice of the present invention, the following recycle method or multi-stage reaction method can be employed.

In the first place, the recycle method will be described.

In the produced solution during or after the reaction, there are included the alcohol as the raw material, the α-hydroxycarboxylate as the product, the α-hydroxycarboxylic(N-alkyl)amide as the by-product, the α-hydroxycarboxylic amide as the raw material, and the catalyst in the order of low boiling points. In the recycle method, this produced solution is introduced into a distillation section, and the unreacted alcohol and the produced α-hydroxycarboxylate are separated as vaporized components. On the other hand, a part or all of the unvaporized material is directly circulated to the reactor as they are, and the α-hydroxycarboxylic amide and the alcohol which are the raw materials are added to the reactor to carry out the reaction again. Since the catalyst can be reused so long as it has activity, the production of the α-hydroxycarboxylate per unit of the catalyst can be increased.

When the by-product α-hydroxycarboxylic(N-alkyl) amide having a lower boiling point than the raw material α-hydroxycarboxylic amide is accumulated and its content increases, a part or all of the unvaporized material which remains in the (first) distillation section is introduced into the second distillation section, in which the α-hydroxycarboxylic(N-alkyl)amide is separated as a vaporized component, and a part or all of the unvaporized material is circulated to the reactor. In addition to the α-hydroxycarboxylic(N-alkyl)amide, the by-products having boiling points between the α-hydroxycarboxylate and the α-hydroxycarboxylic amide can also be removed by this operation. When a large amount of the by-products having higher boiling points than the raw material α-hydroxycarboxylic amide is accumulated, a part or all of the unvaporized material may be drawn out and discarded. In addition, the fresh catalyst may newly be added to the reactor as much as the mol of the catalyst contained in the discarded unvaporized material.

A distillation operation can be accomplished by a usual procedure. The packed column, the plate column or a thin film distillation column can suitably be selected in consideration of used conditions. Either of batch distillation or continuous distillation is practicable. In particular, distillation facilities do not have to be installed independently of the reactor, and a distillation column may be disposed on the reactor, whereby the distillation operation can be carried out while the produced solution is kept in the reactor without any problem. No particular restriction is put on distillation conditions. Pressure can suitably be selected in the wide range of from atmospheric pressure to reduced pressure, and temperature can suitably be selected from temperatures of 250° C. or less at which the quality of a usual organic substance does not change.

Next, the above-mentioned multi-stage reaction method will be described.

In this multi-stage reaction method, a plurality of reaction sections is used, and a gas including ammonia and the alcohol and a liquid including the amide are allowed to flow in a counterflow state, whereby they are brought into contact with each other.

In this method,
(a) the plurality of reaction sections are connected in series, and each reactor is disposed between and connected to the adjacent reaction sections so that the liquid and the gas can flow in the counterflow state,
(b) the α-hydroxycarboxylic amide and the alcohol which are the raw materials are fed to the first or the later reaction section,
(c) the respective reaction sections are kept in a boiling state, and a gas including the alcohol and produced ammonia from a certain reaction section is fed to a previous reaction section, and the reaction solution including the raw material and the product in the reaction section is then fed to the later reaction section, and
(d) the gas is discharged from the first reaction section, and the reaction solution is discharged from the last reaction section.

In the respective reaction sections, the reaction solution is in the boiling state. Here, the boiling state means a state where produced ammonia is vaporized together with the alcohol in the reaction solution. In the respective reaction sections, the raw material amide reacts with the raw material alcohol in the presence of the catalyst to change into an ester. The solution including the produced ester and the raw material amide flows to the next reaction section. That is to say, as the reaction solution progresses to the last reaction section, the conversion of the amide increases, so that the ester increases.

A part of ammonia generated in each reaction section is vaporized together with the alcohol, and then fed to the adjacent reaction section on the upstream side. As the distilled gas progresses from the last reaction section to the first reaction section, the proportion of ammonia in the distilled gas increases. As a result, in each reaction section, there can be maintained a proportional relation between a mol ratio of the amide to the alcohol which are the raw materials in the liquid phase and a molar fraction of ammonia in the distilled gas from the reaction section. Thus, the conversion of the amide can be increased without altering the amount of the distillate in order to keep the boiling state in all the reaction sections by a small amount of heat energy, it is desirable to employ (a) a method which comprises heating the reaction solution in the last reaction section, vaporizing a part of the alcohol or a mixed solution of the alcohol and ammonia, introducing the resultant vapor into the previous reaction section in turn, and then drawing the vapor from the first reaction section, or (b) a method which comprises delivering the vapor of the alcohol or a mixed gas of the alcohol vapor and an inert gas to the last reaction section, introducing the vapor or the gas into the previous reaction section in turn, and then drawing the vapor or the gas from the first reaction section.

The reaction sections may be connected to each other in series, and they do not have to be independent reactors. That is to say, the independent reactors may be connected by pipes, or alternatively one reactor may be divided into a plurality of reaction sections. The stereoscopic arrangement of the reaction sections is not restrictive, and they may be arranged horizontally or vertically. A step column type reactor has a plurality of reaction sections which are vertically connected to each other.

As an example of a device in which the independent reactors are connected by the pipes, a device in which three reactors are connected is shown in FIG. 1. In FIG. 1, the amide which is the raw material is fed to the first reactor 1, and the gas is fed to the third reactor 3. The respective reactors are connected by gas conduits 8, 9 and liquid conduits 4, 5, and the liquid flows from the first reactor 1 to the second reactor 2 and then to the third reactor 3 through the liquid conduits. The gas conversely flows from the third reactor 3 to the second reactor 2 and then to the first reactor 1 through the gas conduits. In the case that one reactor is divided into the plurality of reaction sections, the respective reaction sections are compartmentalized by compartments or the like so that the liquid and the gas may flow in the counterflow state.

In such a multi-stage reaction method, it is important that an operation is performed so that an ammonia concentration in the reaction solution in every reaction section is maintained at 0.1% by weight or less.

The employment of this multi-stage reaction method enables a high conversion and selectivity to be obtained by a small amount of heat energy.

According to the present invention, the α-hydroxycarboxylate can be prepared from the α-hydroxycarboxylic amide and the alcohol with the high conversion and selectivity in an industrially advantageous manner.

Next, the present invention will be described in more detail in accordance with examples, but the scope of the present invention should not be limited at all by these examples.

EXAMPLE 1

65.3 g (0.634 mol) of α-hydroxyisobutyric amide (HBD) was dissolved in 1000 g of isopropanol. To the solution, there was added a solution obtained by dissolving 30 g (0.106 mol) of titanium tetraisopropoxide in 1000 g of isopropanol. The mixed solution was concentrated to 840 g by the use of a rotary evaporator to distill off isopropanol. The condensate was allowed to stand at room temperature one whole day and night, and the deposited precipitate was collected by filtration, washed with heptane, and then vacuum-dried to obtain 37.0 g of complex crystals. The thus obtained complex was subjected to elemental analysis, and the results were Ti=10.5 wt %, C=42.7 wt %, H=7.91 wt % and N=12.1 wt %. This complex was identified as $Ti(HBD)_4$ (calculated values in the elemental analysis: Ti=10.4 wt %, C=41.8 wt %, H=7.83 wt % and N=12.2 wt %).

In a 300 ml stainless steel autoclave equipped with a jacket type reflux condenser and a stirrer were placed 30.0 g (0.291 mol) of α-hydroxyisobutyric amide, 100 g of methanol and 4.85 g (0.0106 mol) of the $Ti(HBD)_4$ complex, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. In this case, an oil at 185° C. was circulated through the jacket of the reflux condenser to heat the reaction solution, whereby a part of methanol was drawn together with ammonia at a rate of 30 g/hr through the upper portion of the reflux condenser. Simultaneously, methanol was fed at a rate of 30 g/hr to the reactor.

After the reaction, the reaction solution was cooled and then analyzed by gas chromatography. As a result, an ammonia concentration in the produced solution was less than 0.01 wt %, an α-hydroxyisobutyric amide conversion was 95.3 mol %, a methyl α-hydroxyisobutyrate selectivity was 97.1 mol %, and an α-hydroxycarboxylic(N-methyl) amide selectivity was 2.9 mol %.

Comparative Example 1

In a 300 ml stainless steel autoclave equipped with a stirrer were placed 30.0 g (0.291 mol) of α-hydroxyisobutyric amide, 100 g of methanol and 4.85 g (0.0106 mol) of $Ti(HBD)_4$ complex, and reaction was carried out at 190° C. for 1.5 hours with stirring in the closed autoclave, pressure being maintained at 3.0 MPa.

An ammonia concentration in the produced solution was less than 1.01 wt %, an α-hydroxyisobutyric amide conversion was 34.9 mol %, a methyl α-hydroxyisobutyrate selectivity was 78.9 mol %, and an α-hydroxycarboxylic(N-methyl)amide selectivity was 18.2 mol %.

Comparative Example 2

In a 300 ml stainless steel autoclave equipped with a jacket type reflux condenser and a stirrer were placed 30.0 g (0.291 mol) of α-hydroxyisobutyric amide, 100 g of methanol and 4.85 g (0.0106 mol) of $Ti(HBD)_4$ complex, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. In this case, cold water at 20° C. was circulated through the jacket of the reflux condenser to cool the reaction solution, whereby all of methanol vaporized in the reactor was condensed. Methanol in which ammonia was dissolved was returned to the reactor.

An ammonia concentration in the produced solution was 0.59 wt %, an α-hydroxyisobutyric amide conversion was 56.4 mol %, a methyl α-hydroxyisobutyrate selectivity was 87.1 mol %, and an α-hydroxycarboxylic(N-methyl)amide selectivity was 11.2 mol %.

EXAMPLE 2

56.5 g (0.634 mol) of lactamide (LD) was dissolved in 500 g of isopropanol. To the solution, there was added a solution obtained by dissolving 30 g (0.106 mol) of titanium tetraisopropoxide in 150 g of isopropanol. The mixed solution was concentrated to 200 g by the use of a rotary evaporator to distill off isopropanol. The condensate was allowed to stand at room temperature one whole day and night, and the deposited precipitate was collected by filtration, washed with heptane, and then vacuum-dried to obtain 34.3 g of complex crystals. The thus obtained complex was subjected to elemental analysis, and the results were Ti=11.9 wt %, C=36.0 wt %, H=6.84 wt % and N=13.6 wt %. This complex was identified as $Ti(LD)_4$ (calculated values in the elemental analysis: Ti=11.9 wt %, C=35.6 wt %, H=6.93 wt % and N=13.9 wt %).

In a 300 ml stainless steel autoclave equipped with a jacket type reflux condenser and a stirrer were placed 25.9 g (0.291 mol) of lactamide, 100 g of methanol and 4.28 g (0.0106 mol) of the $Ti(HBD)_4$ complex, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. In this case, an oil at 185° C. was circulated through the jacket of the reflux condenser to heat the reaction solution, whereby a part of methanol was drawn together with ammonia at a rate of 30 g/hr through the upper portion of the reflux condenser. Simultaneously, methanol was fed at a rate of 30 g/hr to the reactor.

After the reaction, the reaction solution was cooled and then analyzed by gas chromatography. As a result, an ammonia concentration in the produced solution was less than 0.01 wt %, a lactamide conversion was 95.6 mol %, a methyl lactate selectivity was 97.4 mol %, and a lacto(N-methyl)amide selectivity was 2.6 mol %.

EXAMPLE 3

40 g of bismuth nitrate were dissolved in 50 ml of a 10% aqueous nitric acid solution, and a pH of the solution was then adjusted to 8 with a 28 wt % aqueous ammonia to precipitate bismuth hydroxide. This precipitate was collected by filtration, washed with water, dried at 110° C. one whole day and night, and then calcined at 450° C. for 3 hours. Esterification reaction was carried out with methanol in the same manner as in Example 1 except that 3.0 g of the resultant oxide was used as a catalyst.

After the reaction, the reaction solution was cooled and then analyzed by gas chromatography. As a result, an ammonia concentration in the produced solution was less than 0.01 wt %, an α-hydroxyisobutyric amide conversion was 57.3 mol %, a methyl α-hydroxyisobutyrate selectivity was 97.3 mol %, and an α-hydroxyisobutyric(N-methyl)amide selectivity was 2.7 mol %.

Comparative Example 3

Esterification reaction was carried out with methanol in the same manner as in Comparative Example 2 by the use of 3.0 g of bismuth oxide obtained in Example 3 as a catalyst. An ammonia concentration in the produced solution was 0.47 wt %, an α-hydroxyisobutyric amide conversion was 32.7 mol %, a methyl α-hydroxyisobutyrate selectivity was 80.3 mol %, and an α-hydroxyisobutyric(N-methyl)amide selectivity was 19.7 mol %.

EXAMPLE 4

200 g of cerium nitrate was dissolved in 2000 ml of water, and a 5 wt % aqueous ammonium carbonate solution was added to the solution with stirring to adjust a pH of the solution to 8, so that precipitation occurred. This precipitate was collected by filtration, washed with water, dried at 110° C. one whole day and night, and then calcined at 450° C. for 3 hours. Esterification reaction was carried out with methanol in the same manner as in Example 1 except that 3.0 g of the resultant oxide was used as a catalyst.

After the reaction, the reaction solution was cooled and then analyzed by gas chromatography. As a result, an ammonia concentration in the produced solution was less than 0.01 wt %, an α-hydroxyisobutyric amide conversion was 81.7 mol %, a methyl α-hydroxyisobutyrate selectivity was 97.4 mol %, and an α-hydroxyisobutyric(N-methyl)amide selectivity was 2.6 mol %.

Comparative Example 4

Esterification reaction was carried out with methanol in the same manner as in Comparative Example 2 by the use of 3.0 g of cerium oxide obtained in Example 4 as a catalyst. An ammonia concentration in the produced solution was 0.86 wt %, an α-hydroxyisobutyric amide conversion was 52.7 mol %, a methyl α-hydroxyisobutyrate selectivity was 86.5 mol %, and an α-hydroxyisobutyric(N-methyl)amide selectivity was 13.5 mol %.

EXAMPLE 5

Esterification reaction was carried out with methanol in the same manner as in Example 1 except that 2.0 g of a metallic bismuth fine powder was used as a catalyst.

After the reaction, the reaction solution was cooled and then analyzed by gas chromatography. As a result, an ammonia concentration in the produced solution was less than 0.01 wt %, an α-hydroxyisobutyric amide conversion was 64.7 mol %, a methyl α-hydroxyisobutyrate selectivity was 97.3 mol %, and an α-hydroxyisobutyric(N-methyl) amide selectivity was 2.7 mol %.

Comparative Example 5

Esterification reaction was carried out with methanol in the same manner as in Comparative Example 2 by the use of 2.0 g of a metallic bismuth fine powder as a catalyst.

An ammonia concentration in the produced solution was 0.75 wt %, an α-hydroxyisobutyric amide conversion was 47.4 mol %, a methyl α-hydroxyisobutyrate selectivity was 82.6 mol %, and an α-hydroxyisobutyric(N-methyl)amide selectivity was 17.4 mol %.

EXAMPLE 6

Esterification Reaction Experiment

In a 300 ml stainless steel autoclave equipped with a jacket type reflux condenser and a stirrer were placed 30.0 g (0.291 mol) of α-hydroxyisobutyric amide, 100 g of methanol and 4.85 g (0.0106 mol) of Ti(HBD)$_4$ complex formed in the same manner as in Example 1, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. In this case, an oil at 185° C. was circulated through the jacket of the reflux condenser to heat the reaction solution, whereby a part of methanol was drawn together with ammonia at a rate of 50 g/hr through the upper portion of the reflux condenser. Simultaneously, methanol was fed at a rate of 50 g/hr to the reactor. After the reaction, the reaction solution was cooled and then analyzed by gas chromatography. As a result, an ammonia concentration in the produced solution was less than 0.01 wt %, an α-hydroxyisobutyric amide conversion was 95.6 mol %, a methyl α-hydroxyisobutyrate selectivity was 98.5 mol %, and an α-hydroxyisobutyric(N-methyl)amide selectivity was 1.5 mol %.

Recycle Experiment 1

The reaction solution obtained by the esterification reaction experiment was drawn from the reactor, distillation operation was then carried out. 200 ml of the reaction solution was put into an eggplant type flask, and unreacted methanol was separated as a fraction at 65° C. under atmospheric pressure. Next, produced methyl α-hydroxyisobutyrate was separated as a fraction at 50° C. under a reduced pressure of 30 mmHg. The remaining unvaporized material included a part of methyl α-hydroxyisobutyrate which was not collected as the fraction, α-hydroxyisobutyric(N-methyl)amide as a by-product, α-hydroxyisobutyric amide which was the unreacted raw material, and the titanium metallic complex as a catalytic component.

All of the unvaporized material was placed in the reactor, and α-hydroxyisobutyric amide and methanol were added thereto again to perform the esterification reaction. In this case, the total of α-hydroxyisobutyric amide newly added and α-hydroxyisobutyric amide present in the unvaporized material was regulated so as to be 30.0 g. This operation was repeated 10 times. The results are shown in Table 1. The by-production of about 1.5 mol % of α-hydroxyisobutyric (N-methyl)amide was observed every esterification reaction, and in Recycle Experiment 1, α-hydroxyisobutyric(N-methyl)amide tended to be accumulated each time the reaction was repeated.

TABLE 1

| Number of Repeated Batch | HBD Conversion (mol %) | HBM Selectivity (mol %) | N—Me Amide Selectivity (mol %) | Sum of N—Me Amide Selectivity (mol %) |
| --- | --- | --- | --- | --- |
| 1 | 95.6 | 98.5 | 1.5 | 1.5 |
| 2 | 95.3 | 98.4 | 1.6 | 3.1 |
| 3 | 95.2 | 98.6 | 1.4 | 4.5 |
| 4 | 95.2 | 98.5 | 1.5 | 6.0 |
| 5 | 95.3 | 98.4 | 1.6 | 7.6 |
| 6 | 95.5 | 98.6 | 1.4 | 9.0 |
| 7 | 95.4 | 98.5 | 1.5 | 10.4 |
| 8 | 95.4 | 98.5 | 1.5 | 12.0 |
| 9 | 95.3 | 98.4 | 1.6 | 13.6 |
| 10 | 95.1 | 98.6 | 1.4 | 15.0 |

HBD: α-Hydroxyisobutyric amide
HBM: Methyl α-hydroxyisobutyrate
N—Me Amide: α-Hydroxyisobutyric (N-methyl)amide HBD Conversion (mol %)=[1−(mol of unreacted HBD at this batch)/(mol of newly added HBD at this batch+mol of unreacted HBD at previous batch)]×100

HBM Selectivity (mol %)=[(mol of HBM produced at this batch)/(mol of HBM produced at this batch+mol of N—Me amide produced at this batch)]×100

N—Me Amide selectivity (mol %)=[(mol of N—Me amide produced at this batch)/(mol of HBM produced at this batch+mol of N—Me amide produced at this batch)]×100

Sum of N—Me amide selectivity (mol %)=[(mol of N—Me amide contained in solution produced at this batch)/(mol of HBM produced at this batch+mol of N—Me amide produced at this batch)]×100

EXAMPLE 7

The reaction solution produced at the 10th of the experiments repeated in Example 6 was distilled in accordance with the operation of Recycle Experiment 1 in Example 1 to separate unreacted methanol and produced methyl α-hydroxyisobutyrate as fractions. 30% of the unvaporized material was discarded, and the residue, i.e., 70% of the unvaporized material and 1.45 g (0.0032 mol) of Ti(HBD)$_4$ complex were newly placed in a reactor, and α-hydroxyisobutyric amide and methanol were added thereto again to carry out esterification reaction at the 11th batch. The results are shown in Table 2.

The accumulation of α-hydroxyisobutyric(N-methyl) amide could be inhibited by discarding the part of the unvaporized material.

EXAMPLE 8

Recycle Experiment 2

The reaction solution produced at the 11th of the experiments repeated in Example 7 was distilled in accordance with the operation of Recycle Experiment 1 in Example 6 to separate unreacted methanol and produced methyl α-hydroxyisobutyrate as fractions. The resultant unvaporized material was subjected to the second distillation to separate by-procut α-hydroxyisobutyric(N-methyl)amide as a fraction at 100° C. under a reduced pressure of 10 mmHg. The remaining unvaporized material contained α-hydroxyisobutyric amide as an unreacted raw material and a metallic complex of titanium as a catalytic component. All of the unvaporized material was placed in the reactor, and α-hydroxyisobutyric amide and methanol were added thereto again to perform the 12th esterification reaction. The results are shown in Table 2. The accumulation of α-hydroxyisobutyric(N-methyl)amide in a reaction system could be prevented by separating and removing α-hydroxyisobutyric(N-methyl)amide in the second distillation step.

TABLE 2

| Number of Repeated Batch | HBD Conversion (mol %) | HBM Selectivity (mol %) | N—Me Amide Selectivity (mol %) | Sum of N—Me Amide Selectivity (mol %) |
| --- | --- | --- | --- | --- |
| Example 6 10th Batch | 95.1 | 98.6 | 1.4 | 15.0 |
| Example 7 11th Batch | 95.6 | 98.6 | 1.4 | 11.9 |
| Example 8 12th Batch | 95.3 | 98.3 | 1.7 | 1.7 |

EXAMPLE 9

In a 300 ml stainless steel autoclave equipped with a stirrer were placed 25.0 g (0.291 mol) of lactamide, 100 g of methanol and 4.28 g (0.0106 mol) of Ti(LD)$_4$ complex formed in the same manner as in Example 2, and reaction was repeated in the 1st batch to the 5th batch under the esterification reaction conditions in Example 6 in accordance with the procedure of Recycle Experiment 1. In addition, the reaction was repeated at the 6th batch in accordance with the procedure of Recycle Experiment 2 in Example 8.

The results are shown in Table 3.

TABLE 3

| Number of Repeated Batch | HBD Conversion (mol %) | HBM Selectivity (mol %) | N—Me Amide Selectivity (mol %) | Sum of N—Me Amide Selectivity (mol %) |
| --- | --- | --- | --- | --- |
| 1 | 95.4 | 98.2 | 1.8 | 1.8 |
| 2 | 95.3 | 98.3 | 1.7 | 3.5 |
| 3 | 95.2 | 98.1 | 1.9 | 5.4 |
| 4 | 95.3 | 98.5 | 1.5 | 6.9 |
| 5 | 95.1 | 98.4 | 1.8 | 8.7 |
| 6 | 95.2 | 98.2 | 1.8 | 1.8 |

LD: Lactamide
LM: Methyl α-hydroxylactate
N—Me Amide: Lacto(N-methyl)amide

EXAMPLE 10

1800 g of methanol was added to 31.0 g (0.301 mol) of α-hydroxyisobutyric amide (HBD) and 30.0 g (0.120 mol) of dibutyltin oxide, and they were dissolved by heating under reflux. This solution was concentrated to 150 g by the use of a rotary evaporator to distill off methanol. The condensate was allowed to stand at room temperature one whole day and night, and the deposited precipitate was collected by filtration, washed with heptane, and then vacuum-dried to obtain 42.1 g of complex crystals. The thus obtained complex was subjected to elemental analysis, and the results were Sn=24.5 wt %, C=42.1 wt %, H=8.16 wt % and N=5.97 wt %. This complex was identified as (HBD)$_2$Bu$_2$Sn (calculated values in the elemental analysis: Sn=27.1 wt %, C=43.8 wt %, H=8.21 wt % and N=6.38 wt %). In a 300 ml stainless steel autoclave equipped with a stirrer were placed 30.0 g (0.291 mol) of α-hydroxyisobutyric amide, 100 g of methanol and 10.57 g (0.0241 mol) of (HBD)$_2$Bu$_2$Sn complex, and reaction was repeated in the 1st batch to the 5th batch in accordance with the procedure of Recycle Experiment 1 under the esterification reaction conditions in Example 6 except that a reaction time was changed to 2.5 hours. The reaction solution produced in the 5th of the repeated experiments was distilled in accordance with the procedure of Recycle Experiment 1 in Example 6 to separate unreacted methanol and produced methyl α-hydroxyisobutyrate as fractions. 50% of the unvaporized material was fed to the reactor as it was, and the residue, i.e., 50% of the unvaporized material was distilled in accordance with the distillation procedure of Recycle Experiment 2 in Example 8 to separate and remove α-hydroxyisobutyric(N-methyl)amide as a fraction, and this fraction was then fed to the reactor as the unvaporized material of the second distillation. In addition, α-hydroxyisobutyric amide and methanol were added to the reactor to carry out the 6th esterification reaction. The results are shown in Table 4.

TABLE 4

| Number of Repeated Batch | HBD Conversion (mol %) | HBM Selectivity (mol %) | N—Me Amide Selectivity (mol %) | Sum of N—Me Amide Selectivity (mol %) |
| --- | --- | --- | --- | --- |
| 1 | 85.3 | 97.2 | 2.8 | 2.8 |
| 2 | 84.7 | 97.5 | 2.5 | 5.6 |
| 3 | 83.8 | 97.1 | 2.9 | 8.6 |
| 4 | 86.6 | 97.3 | 2.7 | 11.0 |
| 5 | 85.1 | 97.7 | 2.3 | 13.5 |
| 6 | 85.2 | 97.6 | 2.4 | 9.1 |

EXAMPLE 11

Figure 2:
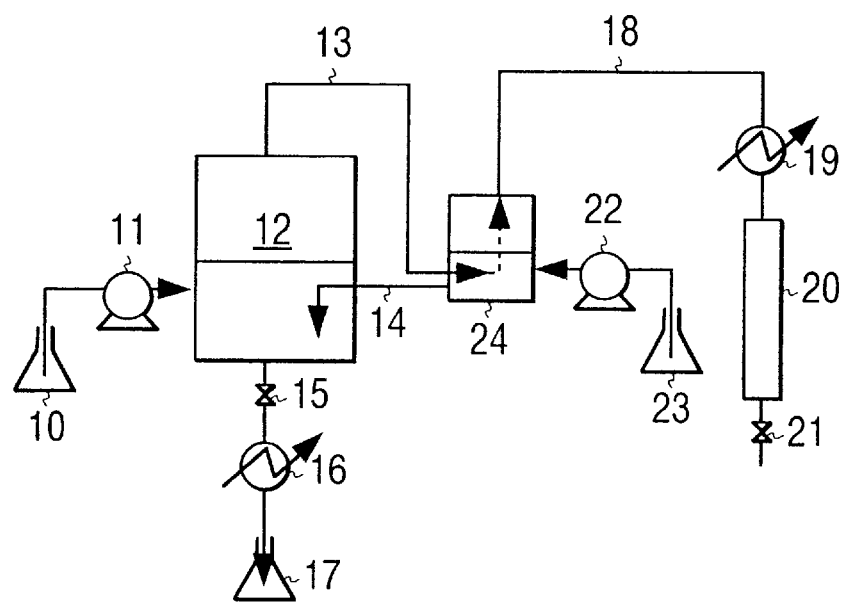
FIG. 2 is a schematic view of the reaction apparatus used in Examples 11 to 15.

A reaction apparatus was prepared in which an upper portion of a 500 ml SUS 316 reactor (a lower reactor) equipped with a forced stirrer was connected to a 150 ml SUS 316 reactor (an upper reactor) so that a liquid and a gas might flow in a counterflow state. The reaction apparatus was constituted so that the lower reactor might be heated to vaporize an internal alcohol, and so that the gas might be drawn through the upper reactor and the liquid in the upper reactor might be drawn through the lower reactor. FIG. 2 shows a schematic view of this reaction apparatus.

To the upper reactor in this reaction apparatus, there were fed α-hydroxyisobutyric amide, methanol and titanium isopropoxide as a catalyst at 50 g/hr, 100 g/hr and 10 g/hr, respectively, by a liquid feed pump. To the lower reactor, methanol was fed at 100 g/hr by the use of the liquid feed pump. The lower reactor was heated to vaporize ammonia and methanol, whereas the temperature of the upper reactor was sufficiently kept to suppress the condensation of methanol vapor coming from the lower reactor to the utmost. A distilled gas from the upper reactor was liquefied by a condenser, and the resultant condensate was then stored in a condensate receiver. In such a constitution, the temperatures of the liquids in the upper reactor and the lower reactor were maintained at 170° C.

A reaction solution and a distillate were obtained from the bottom of the lower reactor and the upper reactor at 141 g/hr and 110 g/hr, respectively. The reaction solution obtained from the lower reactor was analyzed by gas chromatography, and as a result, a conversion of α-hydroxyisobutyric amide was 83 mol %, and methyl α-hydroxyisobutyrate as a product was obtained at a selectivity of 98 mol %. Furthermore, the distilled gas was liquefied by cooling, and then analyzed. As a result, it was apparent that the resultant liquid contained 4.1 wt % of ammonia and 95.9 wt % of methanol. Incidentally, ammonia concentrations in the reaction solution in the lower reactor and the reaction solution in the upper reactor were equal to each other, and it was less than 0.01 wt %.

Reference Example 1

α-Hydroxyisobutyric amide, methanol and titanium isopropoxide as a catalyst were fed to a 500 ml SUS 316 reactor equipped with a forced stirrer at 50 g/hr, 200 g/hr and 10 g/hr, respectively. The reactor was then heated to distill off ammonia and methanol. Reaction solution temperature was maintained at 170° C., and the reaction solution was obtained at 141 g/hr and a distilate was obtained at 110 g/hr.

The reaction solution obtained through the lower portion of the reactor was analyzed by gas chromatography, and as a result, a conversion of α-hydroxyisobutyric amide was 63 mol %, and methyl α-hydroxyisobutyrate as a product was obtained at a selectivity of 98 mol %. Furthermore, the distilled gas was liquefied by cooling, and then analyzed. As a result, it was apparent that the resultant liquid contained 3.4 wt % of ammonia and 96.6 wt % of methanol.

EXAMPLE 12

The same procedure as in Example 11 was conducted except that α-hydroxyisobutyric amide was replaced with lactamide.

A conversion of lactamide was 80 mol %, and a selectivity of methyl lactate was 98 mol %.

EXAMPLE 13

The same procedure as in Example 11 was conducted except that titanium isopropoxide was replaced with dibutyltin oxide.

A conversion of α-hydroxyisobutyric amide was 70 mol %, and a selectivity of methyl α-hydroxyisobutyrate was 98 mol %.

EXAMPLE 14

The same procedure as in Example 11 was conducted except that titanium isopropoxide was replaced with triflate of a lanthanoide.

A conversion of α-hydroxyisobutyric amide was 83 mol %, and a selectivity of methyl α-hydroxyisobutyrate was 8 mol %.

EXAMPLE 15

The same procedure as in Example 11 was conducted except that titanium isopropoxide was replaced with bismuth oxide in a slurry state.

A conversion of α-hydroxyisobutyric amide was 50 mol %, and a selectivity of methyl α-hydroxyisobutyrate was 98 mol %.

EXAMPLE 16

An apparatus was used in which a liquid dispersion type packed column having an inner diameter of 2 cm and a column length of 2 m and packed with Dickson packings having a diameter of 3 mm was connected to the upper portion of a 100 ml stainless steel autoclave, and a mixed solution of 30 wt % of α-hydroxyisobutyric amide, 64 wt % of methanol and 6 wt % of titanium isopropoxide was then fed at 57 g/hr to the column through a position 50 cm away from a column top. Furthermore, methanol was fed at 85 g/hr to the column through a position 50 cm away from the column bottom, and the autoclave was then heated to gasify methanol, whereby a methanol gas including ammonia was stripped through the column top at 62 g/hr. In this case, pressure was maintained at 2 MPa so that reaction solution temperature might be 170° C., and a reaction solution was drawn through the bottom of the autoclave so that the volume of the liquid in the autoclave might be 50 ml.

The reaction solution obtained through the lower portion of the reactor was analyzed by gas chromatography, and as a result, an ammonia concentration in the produced solution was less than 0.01 wt %, an α-hydroxyisobutyric amide conversion was 86 mol %, methyl α-hydroxyisobutyrate as a product was obtained at a selectivity of 97 mol %. In addition, the stripped gas was liquefied by cooling, and the resultant liquid was then analyzed. As a result, the liquid contained 2.7 wt % of ammonia and 97.2 wt % of methanol.

EXAMPLE 17

A bubble column having an inner diameter of 2 cm and a column length of 1 m was used, and a mixed solution of 30 wt % of α-hydroxyisobutyric amide, 64 wt % of methanol and 6 wt % of titanium isopropoxide was then fed at 57 g/hr to the column through a position 25 cm away from the column top. Furthermore, methanol was fed at 85 g/hr to the column through a position 25 cm away from a column bottom, and the bottom of the column was then heated to gasify methanol, whereby a methanol gas including ammonia was stripped through the column tip at 62 g/hr. In this case, pressure was maintained at 2 MPa so that reaction solution temperature might be 170° C., and the reaction solution was drawn through the bottom of the column so that a liquid surface might be constant at a height 10 cm away than a column top.

The reaction solution obtained through the bottom of the reactor was analyzed by gas chromatography, and as a result, an ammonia concentration in the produced solution was less than 0.01 wt %, an α-hydroxyisobutyric amide conversion was 82 mol %, methyl α-hydroxyisobutyrate as a product was obtained at a selectivity of 97 mol %. In addition, the stripped gas was liquefied by cooling, and the resultant liquid was then analyzed. As a result, the liquid contained 2.6 wt % of ammonia and 97.3 wt % of methanol.

EXAMPLE 18

The same procedure as in Example 16 was conducted except that α-hydroxyisobutyric amide was replaced with lactamide.

A conversion of lactamide was 81 mol %, and a selectivity of methyl lactate was 97 mol %.

EXAMPLE 19

The same procedure as in Example 16 was conducted except that titanium isopropoxide was replaced with dibutyltin oxide.

A conversion of α-hydroxyisobutyric amide was 69 mol %, and a selectivity of methyl α-hydroxyisobutyrate was 97 mol %.

EXAMPLE 20

The same procedure as in Example 16 was conducted except that titanium isopropoxide was replaced with triflate of a lanthanoide.

A conversion of α-hydroxyisobutyric amide was 84 mol %, and a selectivity of methyl α-hydroxyisobutyrate was 97 mol %.

EXAMPLE 21

The same procedure as in Example 17 was conducted except that titanium isopropoxide was replaced with bismuth oxide in a slurry state.

A conversion of α-hydroxyisobutyric amide was 50 mol %, and a selectivity of methyl α-hydroxyisobutyrate was 97 mol %.

EXAMPLE 22

The same procedure as in Example 16 was conducted except that titanium isopropoxide was not used and molded articles of $CeO_2$ having a diameter of 3 mm and a length of 5 mm were used as solid catalyst packings in place of Dickson packings.

A conversion of α-hydroxyisobutyric amide was 50 mol %, and a selectivity of methyl α-hydroxyisobutyrate was 97 mol %.

EXAMPLE 23

In a 300 ml stainless steel autoclave equipped with a jacket type reflux condenser and a stirrer were placed 30.0 g (0.291 mol) of α-hydroxyisobutyric amide, 100 g of methanol and 4.85 g (0.0106 mol) of $Ti(HBD)_4$ complex, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. After the reaction, the reaction solution was cooled and then analyzed by gas chromatography. As a result, an ammonia concentration in the produced solution was less than 0.01 wt %, an α-hydroxyisobutyric amide conversion was 78.7 mol %, and a methyl α-hydroxyisobutyrate selectivity was 95.5 mol %.

EXAMPLE 24

In a 300 ml stainless steel autoclave equipped with a stirrer were placed 30.0 g (0.291 mol) of α-hydroxyisobutyric amide, 100 g of methanol and 3.00 g (0.0106 mol) of titanium tetraisopropoxide, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. After the reaction, the reaction solution was cooled, and its part was sampled and then analyzed by gas chromatography to calculate reaction results. In consequence, an ammonia concentration in the produced solution was less than 0.01 wt %, an α-hydroxyisobutyric amide conversion was 83.0 mol %, and a methyl α-hydroxyisobutyrate selectivity was 79.1 mol %. The produced solution was put in a flask and then subjected to simple distillation to distill methanol, methyl α-hydroxyisobutyrate and unreacted α-hydroxyisobutyric amide, so that 4.85 g of an undistilled material remained. For this undistilled material, elemental analysis was carried out, whereby it was identified as $Ti(HBD)_4$. A part of reacted α-hydroxyisobutyric amide was consumed to form a complex with titanium, and in fact, it was understood that the compound was not concerned with the production of methyl α-hydroxyisobutyrate. In view of this, the methyl α-hydroxyisobutyrate selectivity was calculated again, and it was 95.1 mol %.

Reference Example 2

Titanium tetraisopropoxide was added to a methanol solution of α-hydroxyisobutyric amide, a ratio of α-hydroxyisobutyric amide to titanium tetraisopropoxide being changed. This condition was held with stirring for 5 minutes, and after 5 minutes, α-hydroxyisobutyric amide in a mixed solution was quantitatively analyzed. The quantitative analysis of α-hydroxyisobutyric amide in the mixed solution after 5 minutes was carried out in accordance with an internal standard method by the use of gas chromatography. A molar ratio of the amount of actually used α-hydroxyisobutyric amide (HBD) to the amount of actually used titanium tetraisopropoxide (Ti), and a molar ratio of the amount of α-hydroxyisobutyric amide in the mixed solution quantitatively analyzed by the use of the gas chromatography to the amount of actually used titanium tetraisopropoxide were calculated. The results are shown in Table 5.

TABLE 5

| Molar ratio of actually used HBD amount to actually used Ti amount (HBD/Ti molar ratio) | Molar ratio of HBD amount determined by gas chromatography to actually used Ti amount (HBD/Ti molar ratio) |
| --- | --- |
| 2.00 | 0.03 |
| 4.00 | 0.07 |
| 6.00 | 2.04 |
| 8.00 | 4.02 |

As shown in Table 5, if the molar ratio of the HBD amount determined by the gas chromatography to the actually used Ti amount is 4 or less, α-hydroxyisobutyric amide cannot be detected any more, and hence it can be presumed that $Ti(HBD)_4$ is produced.

EXAMPLE 25

In a 300 ml stainless steel autoclave equipped with a stirrer were placed 30.0 g (0.291 mol) of α-hydroxyisobutyric amide, 100 g of methanol and 10.57 g (0.0241 mol) of $(HBD)_2Bu_2Sn$ complex formed in the same manner as in Example 10, and a nitrogen gas was then fed to the autoclave at 190° C. with stirring, pressure being maintained at 3.0 MPa. Reaction was carried out for 2.5 hours while produced ammonia was discharged together with the nitrogen gas from the autoclave. After the reaction, the reaction solution was cooled, and its part was sampled and then analyzed by gas chromatography to calculate reaction results. In consequence, an α-hydroxyisobutyric amide conversion was 74.5 mol %, an ammonia concentration in the produced solution was less than 0.01 wt %, and a methyl α-hydroxyisobutyrate selectivity was 96.1 mol %.

EXAMPLE 26

In a 300 ml stainless steel autoclave equipped with a stirrer were placed 25.9 g (0.291 mol) of lactamide, 100 g of methanol and 4.28 g (0.0106 mol) of $Ti(LD)_4$ complex formed in the same manner as in Example 2, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. After the reaction, the reaction solution was cooled, and then analyzed by gas chromatography. In consequence, an ammonia concentration in the produced solution was less than 0.01 wt %, a lactamide conversion was 78.1 mol %, and a methyl lactate selectivity was 95.4 mol %.

EXAMPLE 27

In a 300 ml stainless steel autoclave equipped with a jacket type reflux condenser and a stirrer were placed 30.0 g (0.291 mol) of α-hydroxyisobutyric amide, 100 g of methanol and 6.19 g (0.0106 mol) of lanthanum triflate, and a nitrogen gas was then fed to the autoclave at 190° C. with stirring, pressure being maintained at 3.0 MPa. Reaction was carried out for 1.5 hours while produced ammonia was discharged together with the nitrogen gas from the autoclave. In this case, an oil at 185° C. was circulated through the jacket of the reflux condenser to heat the reaction solution, whereby a part of methanol was drawn together with ammonia at a rate of 30 g/hr through the upper portion of the reflux condenser. Simultaneously, methanol was fed at a rate of 30 g/hr to the reactor.

After the reaction, the reaction solution was cooled and then analyzed by gas chromatography. As a result, an ammonia concentration in the produced solution was less than 0.01 wt %, an α-hydroxyisobutyric amide conversion was 98.5 mol %, and a methyl α-hydroxyisobutyrate selectivity was 98.2 mol %.

EXAMPLES 28 TO 32

Each reaction was carried out by the same procedure as in Example 27 except that metallic triflate catalysts described in the following Table 6 were used. The results are shown in Table 6.

TABLE 6

| Example | Catalyst | Amount of Catalyst (g) | α-Hydroxy-isobutyric Amide Conversion (%) | Methyl α-Hydroxy-isobutyrate Selectivity (%) | Methyl α-Hydroxy-isobutyrate Yield (%) |
| --- | --- | --- | --- | --- | --- |
| 27 | $La(OTf)_3$ | 6.19 | 98.5 | 98.2 | 96.7 |
| 28 | $Yb(OTf)_3$ | 6.55 | 98.2 | 97.5 | 95.7 |
| 29 | $Sn(OTf)_3$ | 4.40 | 97.9 | 98.3 | 96.2 |
| 30 | $Mg(OTf)_3$ | 3.40 | 85.3 | 96.5 | 82.3 |
| 31 | $SC(OTf)_3$ | 5.19 | 96.5 | 97.2 | 93.8 |
| 32 | $Zn(OTf)_3$ | 3.84 | 97.1 | 97.7 | 94.9 |

$La(OTf)_3$: Lanthanum triflate, and OTf is the abbreviation of triflate.

Reference Examples 3 to 7

Each reaction was carried out, using metallic carboxylates mentioned in the following Table 7 as catalysts in a mol number equal to that of metallic triflate. The reaction was carried out in the same manner as in Example 27 except that the mentioned catalysts were used. The results are shown in Table 7.

As understood from Table 7, when the metallic triflate was used, the conversion was higher.

TABLE 7

| Example | Catalyst | Amount of Catalyst (g) | α-Hydroxy-isobutyric Amide Conversion (%) | Methyl α-Hydroxy-isobutyrate Selectivity (%) | Methyl α-Hydroxy-isobutyrate Yield (%) |
| --- | --- | --- | --- | --- | --- |
| 3 | $La(OAc)_3 \cdot 1.5H_2O$ | 3.62 | 89.2 | 96.7 | 86.3 |
| 4 | $Yb(OAc)_3 \cdot 4H_2O$ | 4.46 | 88.2 | 95.2 | 83.8 |
| 5 | $Sn(OAc)_3$ | 2.50 | 90.6 | 97.0 | 87.9 |
| 6 | $Mg(OAc)_3 \cdot 4H_2O$ | 2.26 | 75.4 | 95.4 | 71.9 |

TABLE 7-continued

| Example | Catalyst | Amount of Catalyst (g) | α-Hydroxy-isobutyric Amide Conversion (%) | Methyl α-Hydroxy-isobutyrate Selectivity (%) | Yield (%) |
|---|---|---|---|---|---|
| 7 | Zn(OAc)$_3$·2H$_2$O | 2.32 | 86.7 | 94.1 | 81.6 |

La(OAc)$_3$·1.5H$_2$O: Lanthanum carboxylate, and OAC is the carboxylate.

Reference Example 8
(Example Using a Titanium Homogeneous System Catalyst)

Reaction was carried out by the same procedure as in Example 27 except that 5 wt % of water was added as a feed material to α-hydroxyisobutyric amide and 4.85 g (0.0106 mol) of Ti(HBD)$_4$ complex was used as a catalyst.

In this case, an α-hydroxyisobutyric amide conversion was 80.7 mol %, a methyl α-hydroxyisobutyrate selectivity was 90.2 mol %, and an α-hydroxyisobutyric acid selectivity was 8.2 mol %. In the produced solution, a white precipitate was deposited, and it can be presumed that Ti(HBD)$_4$ complex was hydrolyzed during the reaction to partially change into titanium hydroxide and titanium oxide. In consequence, the amide conversion deteriorated, and the hydrolysis of the amide was also accelerated, with the result that the ester selectivity deteriorated.

EXAMPLE 33

Reaction was carried out by the same procedure as in Example 27 except that 5 wt % of water was added as a feed material to α-hydroxyisobutyric amide and 6.19 g (0.0106 mol) of La(OTf)$_3$ was used as a catalyst.

In this case, an α-hydroxyisobutyric amide conversion was 98.2 mol %, and a methyl α-hydroxyisobutyrate selectivity was 97.9 mol %. Hydrolysis toward α-hydroxyisobutyric acid partially occurred owing to water in the system, but since the catalyst was not deactivated, esterification with methanol also simultaneously occurred, so that the deterioration of the ester selectivity was not observed.

EXAMPLE 34

Reaction was carried out by the same procedure as in Example 27 except that 5 wt % of water was added as a feed material to α-hydroxyisobutyric amide and 6.55 g (0.0106 mol) of Yb(OTf)$_3$ was used as a catalyst.

In this case, an α-hydroxyisobutyric amide conversion was 97.3 mol %, and a methyl α-hydroxyisobutyrate selectivity was 97.1 mol %.

EXAMPLE 35

Reaction was carried out by the same procedure as in Example 27 except that 25.9 g (0.291 mol) of lactamide, 100 g of methanol and 6.19 g (0.0106 mol) of La(OTf)$_3$ were used as feed materials.

In this case, a lactamide conversion was 98.1 mol %, and a methyl α-hydroxyisobutyrate selectivity was 97.4 mol %.

EXAMPLE 36

Reaction was carried out by the same procedure as in Example 27 except that 25.9 g (0.291 mol) of lactamide, 100 g of methanol and 6.55 g (0.0106 mol) of Yb(OTf)$_3$ were used as feed materials.

In this case, a lactamide conversion was 96.2 mol %, and a methyl α-hydroxyisobutyrate selectivity was 98.4 mol %.

EXAMPLE 37

Reaction was carried out by the same procedure as in Example 27 except that 25.9 g (0.291 mol) of lactamide, 100 g of methanol and 4.40 g (0.0106 mol) of Sn(OTf)$_3$ were used as feed materials.

In this case, a lactamide conversion was 97.5 mol %, and a methyl α-hydroxyisobutyrate selectivity was 98.7 mol %.

What is claimed is:

1. A process for preparing an α-hydroxycarboxylate which comprises the step of reacting an α-hydroxycarboxylic amide and an alcohol in the presence of a catalyst in a liquid phase, while an ammonia concentration in a reaction solution is maintained at 0.1% by weight or less by discharging generated ammonia as a gas into a gaseous phase, wherein the reaction solution is drawn from a reactor and introduced into a first distillation section; the unreacted alcohol and the produced α-hydroxycarboxylate are separated as vaporized components; a part or all of the unvaporized material is introduced into a second distillation section; an α-hydroxycarboxylic(N-alkyl) amide is separated as a vaporized component; and a part or all of the unvaporized material is circulated to the reactor.

2. The preparation process according to claim 1 wherein generated ammonia is discharged as the gas into the gaseous phase by either or both of steps of bringing the reaction solution into a boiling state and bubbling an inert gas in the reaction solution.

3. The preparation process according to claim 1 wherein the alcohol is continuously fed to the reaction solution, and simultaneously, generated ammonia is discharged together with the alcohol.

4. The preparation process according to claim 1 wherein a gas stripping column is used as a reaction apparatus to discharge a gas including the alcohol and secondarily produced ammonia.

5. The preparation process according to claim 4 wherein the gas stripping column is a packed column, a bubble column or a plate column.

6. The preparation process according to claim 1 wherein
   (a) the plurality of reaction sections are connected in series, and each reactor is disposed between and connected to the adjacent reaction sections so that the liquid and the gas can flow in a counterflow state,
   (b) the α-hydroxycarboxylic amide and the alcohol which are the raw materials are fed to the first or a later reaction section,
   (c) the respective reaction sections are kept in a boiling state, and a gas including the alcohol and secondarily produced ammonia from a certain reaction section is fed to a previous reaction section, and the reaction solution including the raw material and the product in the reaction section is then fed to the later reaction section, and
   (d) the gas is discharged from the first reaction section, and the reaction solution is discharged from the last reaction section.

7. The preparation process according to claim 6 wherein the ammonia concentration in the reaction solution in every reaction section is maintained at 0.1 wt % or less.

8. The preparation process according to claim 1 wherein the α-hydroxycarboxylic amide is lactamide or α-hydroxyisobutyric amide, and the alcohol is methanol.

9. The preparation process according to claim 1 wherein the catalyst is a soluble metallic complex comprising either or both of titanium and tin, and the α-hydroxycarboxylic amide.

10. The preparation process according to claim 1 wherein the catalyst is a metallic trifluoromethanesulfonate.

11. The preparation process according to claim 10 wherein a metal constituting the metallic trifluoromethanesulfonate is at least one selected from the group consisting of elements in the groups 1, 2, 3, 4, 11, 12, 13 and 14 in the periodic table.

12. The preparation process according to claim 11 wherein the metal constituting the metallic trifluoromethanesulfonate is at least one selected from lanthanoides.

13. The preparation process according to claim 1 wherein the catalyst is an insoluble metallic oxide including at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi.

14. The preparation process according to claim 1 wherein the catalyst is an insoluble metal including at least one element selected from the group consisting of Ti, Zr, Hf, V, Nb, Ta, Cr, Mo, W, Fe, Co, Ni, Cu, Ga, In, Bi and Te.

15. The preparation process according to claim 1, wherein the ammonia concentration in the reaction solution is maintained at less than 0.01% by weight during the step of reacting.

16. The preparation process according to claim 1, wherein the ammonia concentration in the reaction solution is continuously maintained at 0.1% by weight or less during the step of reacting.

17. The preparation process according to claim 1, wherein the α-hydroxycarboxylic amide is selected from the group consisting of lactamide and α-hydroxyisobutyric amide, and the alcohol is selected from the group consisting of methanol, ethanol, propanol, butanol, 2-ethylhexanol, glycidyl alcohol and benzyl alcohol.

18. The preparation process according to claim 17, wherein the ammonia concentration in the reaction solution is maintained at less than 0.01% by weight during the step of reacting.

* * * * *